US00PP21814P2

(12) United States Plant Patent

Kako et al.

(10) Patent No.: US PP21,814 P2
(45) Date of Patent: Mar. 22, 2011

(54) *TORENIA* PLANT NAMED 'SUNRENIKONHO'
(50) Latin Name: *Torenia* sp.
Varietal Denomination: Sunrenikonho

(75) Inventors: Tetsuya Kako, Shiga (JP); Kiyoshi Miyazaki, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/590,019

(22) Filed: Oct. 30, 2009

(51) Int. Cl.
*A01H 5/00* (2006.01)

(52) U.S. Cl. ..... Plt./487
(58) Field of Classification Search ..... Plt./263, Plt./487

See application file for complete search history.

*Primary Examiner*—Susan B McCormick Ewoldt
(74) *Attorney, Agent, or Firm*—C. A. Whealy

(57) ABSTRACT

A new and distinct cultivar of *Torenia* plant named 'Sunrenikonho', characterized by its compact and mounding to trailing plant habit; freely branching habit; freely flowering habit; long flowering period; white-colored flowers and good garden performance.

1 Drawing Sheet

Botanical designation: *Torenia* sp.
Cultivar denomination: 'SUNRENIKONHO'.

CROSS-REFERENCED TO CLOSELY RELATED APPLICATIONS

Title: *Torenia* Plant Named 'Sunrenikonpe'
Applicants: Tetsuya Kako & Kiyoshi Miyazaki
Filed: Concurrently with this application (U.S. Plant patent application Ser. No. 12/590,020)

BACKGROUND OF THE INVENTION

The present invention relates to a new and distinct cultivar of *Torenia* plant, botanically known as *Torenia* sp. and hereinafter referred to by the name 'Sunrenikonho'.

The new *Torenia* plant is a product of a planned breeding program conducted by the Inventors in Higashiomi, Shiga, Japan. The objective of the breeding program is to develop new freely-branching *Torenia* plants with mounding habit and numerous large flowers.

The new *Torenia* plant originated from a cross-pollination conducted by the Inventors in Higashiomi, Shiga, Japan in July, 2006 of a proprietary selection of *Torenia* sp, identified as code number TP-1, not patented, as the female, or seed, parent with a proprietary selection of *Torenia* sp. identified as code number TFOEx-W, not patented, as the male, or pollen, parent. The new *Torenia* plant was discovered and selected by the Inventor as a single flowering plant from within the progeny of the stated cross-pollination in a controlled greenhouse environment in Higashiomi, Shiga, Japan in March, 2007.

Asexual reproduction of the new *Torenia* plant by vegetative cuttings in a controlled greenhouse environment in Higashiomi, Shiga, Japan since April, 2007, has shown that the unique features of this new *Torenia* plant are stable and reproduced true to type in successive generations.

SUMMARY OF THE INVENTION

Plants of the new *Torenia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunrenikonho'. These characteristics in combination distinguish 'Sunrenikonho' as a new and distinct cultivar of *Torenia:*

1. Compact and mounding to trailing plant habit.
2. Freely branching habit.
3. Freely flowering habit.
4. Long flowering period.
5. White-colored flowers.
6. Good garden performance.

Plants of the new *Torenia* differ primarily from plants of the female parent selection in the following characteristics:

1. Plants of the new *Torenia* are more mounding than plants of the female parent selection.
2. Plants of the new *Torenia* and the female parent selection differ in flower color as plants of the female parent selection have light purple-colored flowers.

Plants of the new *Torenia* differ primarily from plants of the male parent selection in the following characteristics:

1. Plants of the new *Torenia* are more mounding and trailing than plants of the male parent selection.
2. Plants of the new *Torenia* and the male parent selection differ in flower color as plants of the male parent selection have pink-colored flowers.

Plants of the new *Torenia* can be compared to plants of *Torenia* sp. 'Sunrenikonpe', disclosed in a U.S. Plant patent application Ser. No. 12/590,020, filed concurrently. Plants of the new *Torenia* and 'Sunrenikonpe' differ primarily in flower color as plants of 'Sunrenikonpe' have light violet-colored flowers.

Plants of the new *Torenia* can also be compared to plants of *Torenia* 'Dantorwhite', disclosed in U.S. Plant Pat. No. 16,304. In side-by-side comparisons conducted in Higashiomi, Shiga, Japan, plants of the new *Torenia* and 'Dantorwhite' differed in the following characteristics:

1. Plants of the new *Torenia* had larger leaves than plants of 'Dantorwhite'.

2. Flowers of plants of the new *Torenia* had a smaller and less conspicuous yellow-colored blotch than flowers of plants of 'Dantorwhite'.
3. Plants of the new *Torenia* had thicker peduncles than plants of 'Dantorwhite'.

BRIEF DESCRIPTION OF THE PHOTOGRAPHS

The accompanying colored photographs illustrate the overall appearance of the new *Torenia* plant, showing the colors as true as it is reasonably possible to obtain in colored reproductions of this type. Colors in the photographs may differ slightly from the color values cited in the detailed botanical description which accurately describe the colors of the new *Torenia* plant.

The photograph at the top of the sheet comprises a side perspective view of a typical flowering plant of 'Sunrenikonho' grown in a container.

The photograph at the bottom of the sheet is a close-up view of typical flowers, flower buds and leaves of 'Sunrenikonho'.

DETAILED BOTANICAL DESCRIPTION

The aforementioned photographs and following observations, measurements and values describe plants grown in Higashiomi, Shiga, Japan, under commercial practice during the summer in 15-cm containers in an outdoor nursery with day temperatures averaging 23° C. and night temperatures averaging 15° C. Plants were five and six months old when the photographs and description, respectively, were taken. In the following description, color references are made to The Royal Horticultural Society Colour Chart, 2001 Edition, except where general terms of ordinary dictionary significance are used.

Botanical classification: *Torenia* sp. 'Sunrenikonho'.

Parentage:

*Female, or seed, parent.*—Proprietary selection of *Torenia* sp, identified as code number TP-1, not patented.

*Male, or pollen, parent.*—Proprietary selection of *Torenia* sp. identified as code number TFOEx-W, not patented.

Propagation:

*Type.*—By vegetative cuttings.

*Time to initiate roots.*—About one week at 20° C. to 25° C.

*Time to produce a rooted young plant roots.*—About three to four weeks at 15° C. to 20° C.

*Root description.*—Fibrous; white in color.

*Rooting habit.*—Freely branching.

Plant description:

*Plant form/habit.*—Compact and mounded to trailing plant habit; outwardly spreading; vigorous growth habit; freely branching habit with numerous lateral branches developing per plant, pinching enhances branching potential.

*Plant height.*—About 18.4 cm.

*Plant width (spread).*—About 52 cm.

*Lateral branches.*—Length: About 22.6 cm. Diameter: About 2.6 mm. Internode length: About 4 cm to 9 cm. Aspect: Upright to decumbent. Texture: Sparsely pubescent. Color: Close to 144A.

Foliage description:

*Arrangement.*—Opposite, simple.

*Length.*—About 4.1 cm.

*Width.*—About 3.2 cm.

*Shape.*—Broadly ovate.

*Apex.*—Acute.

*Base.*—Truncate to cordate.

*Margin.*—Serrate.

*Texture, upper surface.*—Pubescent.

*Texture, lower surface.*—Smooth, glabrous.

*Venation pattern.*—Pinnate; reticulate.

*Color.*—Developing leaves, upper surface: Close to 137C. Developing leaves, lower surface: Close to 144B. Fully expanded leaves, upper surface: Close to 137B; venation, close to 145A. Fully expanded leaves, lower surface: Close to 138B; venation, close to 145A.

*Petiole.*—Length: About 8.2 mm. Diameter: About 1.2 mm. Texture, upper and lower surfaces: Smooth, glabrous. Color, upper and lower surfaces: Close to 145A.

Flower description:

*Flower type/habit.*—Single flowers borne in upper leaf axils; corolla bilabiate and calyx tubular; flowers face obliquely upright; freely flowering habit with about 162 flowers developing per plant.

*Fragrance.*—None detected.

*Natural flowering season.*—Plants begin flowering about three to four weeks after planting; long flowering period; continuously flowering from early summer to late autumn in Japan.

*Postproduction longevity.*—Flowers last about four days on the plant.

*Flower buds.*—Height: About 1.5 cm. Diameter: About 7.3 mm. Shape: Ellipsoidal. Color: Close to 144A to 144B.

*Flower diameter.*—About 3.7 cm by 2.9 cm.

*Flower depth.*—About 4 cm.

*Throat diameter.*—About 9.3 mm.

*Tube diameter, base.*—About 3.2 mm.

*Tube length.*—About 2.7 cm.

*Petals.*—Quantity per flower: Bilabiate with one upper or banner petal and one lower petal with two lateral and one lower lobes, petals fused. Upper petal: Length: About 1.6 cm. Width: About 2.4 cm. Shape: Elliptic. Apex: Mucronate to truncate. Margin: Entire; undulating. Texture, upper and lower surfaces: Smooth, glabrous. Color: Developing, upper surface: Close to 155C; towards the throat, close to 91D. Developing, lower surface: Close to 155C. Fully developed, upper and lower surfaces: Close to 155C. Lower petal: Length, lateral and lower lobes: About 1.1 cm. Width, lateral and lower lobes: About 1.7 cm. Shape, lateral and lower lobes: Elliptic. Apex, lateral lobes: Truncate. Apex, lower lobe: Truncate to rounded. Margin, lateral and lower lobes: Entire. Texture, upper and lower surfaces, lateral and lower lobes: Smooth, glabrous. Color, lateral lobes: Developing, upper and lower surfaces: Close to 155C. Fully developed, upper and lower surfaces: Close to 155C. Color, lower lobes: Developing and fully developed, upper surface: Close to 155C; small and weakly conspicuous blotch, close to 3B to 3C. Developing and fully developed, lower surface: Close to 155C. Throat color: Close to 155C; towards the base, close to 12A. Tube color: Close to 155C; towards the base, close to 11C.

*Sepals.*—Quantity per flower: Typically five, fused; margins winged. Calyx length: About 1.75 cm. Calyx diameter: About 7.7 mm. Texture, upper and lower surfaces: Smooth, glabrous. Color, immature, upper and lower surfaces: Close to 144B. Color, mature, upper and lower surfaces: Close to 144A.

*Peduncles.*—Length: About 1.6 cm. Diameter: About 1.3 mm. Texture: Smooth, glabrous. Color: Close to 144A.

*Reproductive organs.*—Stamens: Quantity per flower: Typically four; two pairs of fused anthers. Filament length: About 5 mm to 13 mm. Anther shape: Ellipsoidal. Anther size: About 4 mm by 0.7 mm. Anther color: Close to 155B. Pollen amount: Scarce. Pollen color: Close to 11B. Pistils: Quantity per flower: One. Pistil length: About 2.8 cm. Stigma shape: Elliptic. Stigma color: Close to 155B. Style color: Between 155B to 145C. Ovary color: Close to 144A.

*Seed/fruit.*—Seed and fruit development have not been observed on plants of the new *Torenia*.

Disease/pest resistance: Plants of the new *Torenia* have not been noted to be resistant to pathogens and pests common to *Torenia*.

Garden performance: Plants of the new *Torenia* have been observed to have good garden performance and to tolerate rain, wind and temperatures from about 5° C. to about 30° C.

It is claimed:

1. A new and distinct *Torenia* plant named 'Sunrenikonho' as illustrated and described.

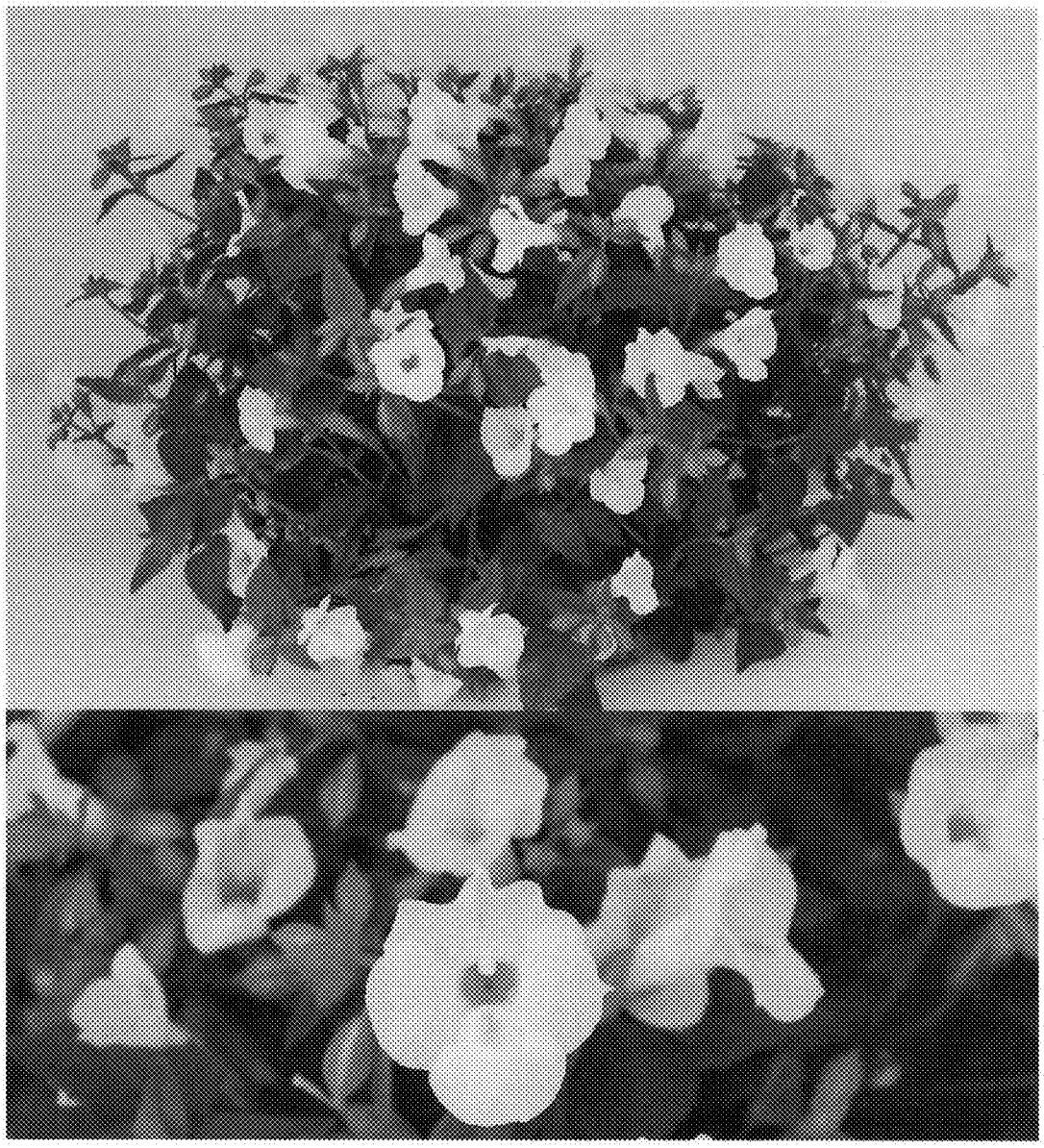

* * * * *